United States Patent [19]

Farng et al.

[11] Patent Number: 4,820,430
[45] Date of Patent: Apr. 11, 1989

[54] COPPER SALTS OF THIODIPROPIONIC ACID DERIVATIVES AS ANTIOXIDANT ADDITIVES AND LUBRICANT COMPOSITIONS THEREOF

[75] Inventors: Liehpao O. Farng, Lawrenceville; Andrew G. Horodysky, Cherry Hill, both of N.J.

[73] Assignee: Mobil Oil Corporation, New York, N.Y.

[21] Appl. No.: 79,186

[22] Filed: Jul. 29, 1987

[51] Int. Cl.[4] .......................................... C10M 105/22
[52] U.S. Cl. .................................... 252/48.6; 252/48.2
[58] Field of Search ................. 252/48.6, 47.5, 51.5 R

[56] References Cited

U.S. PATENT DOCUMENTS

| | | | |
|---|---|---|---|
| 3,296,136 | 1/1967 | Eickemeyer | 252/47.5 |
| 3,422,014 | 1/1969 | Forbes | 252/49.7 |
| 3,869,423 | 3/1975 | Minagawa | 252/51.5 R X |
| 4,110,234 | 8/1978 | Loveless | 252/47.5 |

Primary Examiner—William R. Dixon, Jr.
Assistant Examiner—James M. Hunter, Jr.
Attorney, Agent, or Firm—Alexander J. McKillop; Charles J. Speciale; Howard M. Flournoy

[57] ABSTRACT

Copper salts of thiodipropionic acid derivatives provide excellent multifunctional/antioxidant characteristics for lubricant compositions when incorporated therein.

13 Claims, No Drawings

COPPER SALTS OF THIODIPROPIONIC ACID DERIVATIVES AS ANTIOXIDANT ADDITIVES AND LUBRICANT COMPOSITIONS THEREOF

BACKGROUND OF THE INVENTION

This invention is directed to lubricant compositions containing small additive concentrations of copper salts of thiodipropionic acid derivatives, the copper salts themselves and to their use as multifunctional antioxidant additives in lubricants and similar oleaginous fluids.

The use of sulfur compounds such as thioesters, dithiocarbamates, dithiophosphates, sulfurized olefins, sulfurized oils, and sulfurized fatty acid esters, have been well known for their antioxidant properties, as well as their antiwear, EP characteristics in a variety of products.

The use of copper carboxylates such as copper oleate has been reportedly used as an antioxidant by Exxon Corporation in British Pat. No. 2,056,482 and in European Pat. No. 92946 as an engine oil antioxidant.

The use of thiodipropionic esters such as dilauryl thiodipropionate are well known for their antioxidant properties in a thiodipropioniate are well known for their antioxidant properties in a variety of products including rubbers, plastics and lubricants.

It has now been found that the use of thiodipropionic acid derived copper salts in accordance with the invention provide exceptional multifunctional antioxidant activity, with potential anticorrosion, antiwear, and EP properties. The antioxidant activity demonstrated is greater than that reported for corresponding copper carboxylates or sulfur-containing compounds.

SUMMARY OF THE INVENTION

This invention is directed to improved lubricant compositions comprising minor amounts of a copper salt of a thiodipropionic acid derivative sufficient to impart multifunctional, including antioxidant, characteristics thereto, and a major amount of a lubricant comprising an oil of lubricating viscosity or grease or other solid lubricant prepared therefrom. This invention is also directed to lubricant additive products prepared by reacting a thiodipropionic acid and/or its derivatives with a corresponding copper salt and their use as additives in lubricant compositions. This invention is also directed to liquid hydrocarbyl fuels containing the hereindisclosed thiodipropionic acid derived copper salts.

DESCRIPTION OF PREFERRED EMBODIMENTS

It has now been found as disclosed more specifically hereinbelow that lubricant compositions containing small additive concentrations of copper salts of thiodipropionic acid derivatives, such as cupric thiodipropionate, possess excellent antioxidant activity. Both the copper carboxylate and the thioester moieties are believed to provide the basis for internal synergistic antioxidant activity. The carboxylate group is also believed to contribute additional antirust properties to the additive. These beneficial properties are believed to be enhanced as a result of this novel internal synergism. This internal synergism concept is believed to be applicable to similar structures containing both (a) thioester and (b) copper carboxylate groups within the same molecule. These remarkable benefits are also expected for a variety of synthetic and mineral oil based lubricants. To the best of our knowledge, these compositions have not been previously used in lubricating oils, greases or fuel applications.

Generally speaking, the copper salts are prepared as indicated below.

3,3'-Thiodipropionic acid, for example, and its derivatives were converted to their corresponding copper salts by reaction with almost molar quantities, or less than molar quantities, or more than molar quantities of Cu(I) or Cu(II) ions to make neutral, acidic, or basic salts, Equation (1). Generally, the copper compounds used in this invention can be cupric acetate hydrate, basic cupric acetate, cupric carbonate, basic cupric carbonate, cuprous hydroxide and cupric hydroxife, and other similar copper compounds.

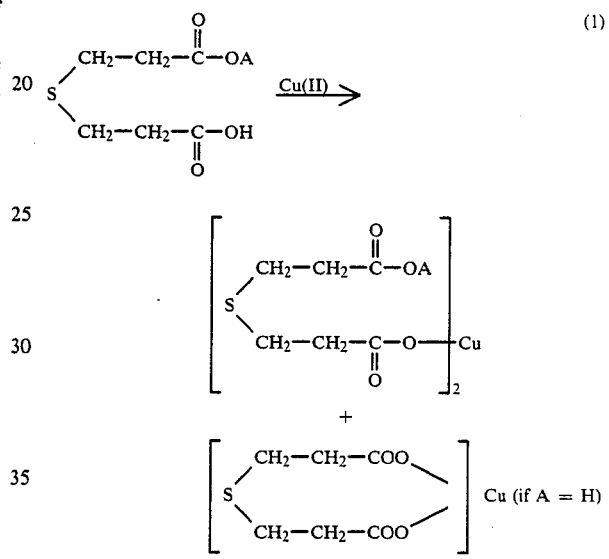

where A is Hydrogen or hydrocarbyl groups containing 1 to 30 carbon atoms or aralkyl groups, or cycloalkyl groups; or hydrocarbyl groups containing unsaturated vinyl or acetylene groups, or hetero groups, such as nitrogen, oxygen and sulfur containing groups.

Thiodipropionic acid derivatives may be readily prepared by any convenient manner, for example, reacting thiodipropionic acids with alcoholic and/or amine containing compounds.

Reaction temperatures and pressures for making both the thiodipropionic acid derivatives and the copper salts may vary from about $-20°$ C. to $300°$ C., preferably $+20°$ C. to about $150°$ C. with pressures from ambient or autogenous to higher if desired and the reaction time can be as little as 1½ hours to 24 hours or more depending, of course, on such variables as temperature, pressure and specific reactants. The acid derivatives, however, may prepared in the presence or absence of a solvent or the presence or absence of a catalyst. When a catalyst or solvent is used in prearation of the acid derivatives, preferred catalyst is p-toluenesulfonic acid or any suitable hydrocarbon solvent, such as toluene, xylene and methanol. Usually no catalyst is used or needed in the reaction between the acid derivative and the copper compound.

The additives of the present invention may be used in mineral or synthetic oils or mixtures of mineral and synthetic oils. In general, mineral oils, both paraffinic, naphthenic and mixtures thereof may be of any suitable lubricating viscosity range, as for example, from about 45 SSU at 100° F. to about 6000 SSU at 100° F. and preferably from about 50 to about 250 SSU at 210° F. These oils may have viscosity indexes ranging to about 100 or higher. Viscosity indexes from about 70 to about 95 are preferred. The average molecular weights of these oils may range from about 250 to about 800. These oils are highly useful as gear oil. In making the grease, the lubricating oil from which it is prepared is generally employed in an amount sufficient to balance the total grease composition, after accounting for the desired quantity of the thickening agent, and other additive components to be included in the grease formulation. Suitable alcohols or alcoholic compounds nclude but are not limited to oleyl alcohol, glycerol monooleate, glycerol dioleate, and mixtures thereof.

In instances where synthetic oils are desired, in preference to mineral oils, various compounds of this type may be successfully utilized. Typical synthetic vehicles include polyisobutylene, polybutenes, hydrogenated polydecenes, polypropylene glycol, polyethylene glycol, trimethylol propane esters, neopentyl and pentaerythritol esters, di(2-ethylhexyl)sebacate, di(2-ethylhexyl)adipate, dibutyl phthalate, fluorocarbons, silicate esters, silanes, esters of phosphorus-containing acids, liquid ureas, ferrocene derivatives, hydrogenated synthetic oils, chain-type polyphenyls, siloxanes and silicones (polysiloxanes), alkyl-substituted diphenyl ethers typified by a butyl-substituted bis(p-phenoxy phenyl)ether, phenoxy phenylethers.

The copper salts of the present invention may be employed in any amount which is effective for imparting the desired degree of oxidation improvement. In many applications, however, the additive product is effectively employed in amounts from 0.01 to 10% by weight or more, and preferably from about 0.1 to 5% of the total weight of the composition. It is understood that other additive products such as antiwear agents, metal passivators and the like may be used for their intended purposes with the present copper salts without deleterious effect.

The following examples present illustrations of the present invention and are not meant to limit it in any way.

EXAMPLE 1

Cupric 3,3'-thiodipropionate was prepared by metathesis of alcoholic copper (II) acetate with an alcoholic solution of the appropriate acid as follows: 53.4 g of the 3,3'-thiodipropionic acid and 1000 ml of absolute methanol were placed in a 2000 ml Erlenmyer flask with agitation. Slowly, 60 g of cupric acetate monohydrate $(Cu(C_2H_3O_2)_2.H_2O)$ was added to the stirred reactants and the entire solution was mixed at ambient temperature over a course of eighteen hours. The resulting precipitants were filtered off and washed with water (600 ml), until free from excess precipitant, and with a little alcohol (100 ml) to remove free acids. It was then oven dried to obtain the desired salts (65.4 g). The product has a blue color and contains 25.6% of copper (Theory: 26.5%).

EXAMPLE 2

Approximately 268.5 g of oleyl alcohol (obtained commercially with 85% purity, 1.0 mole), 300 ml toluene, and 124.6 g of 3,3'-thiodipropionic acid (0.7 mole), were reacted at 114±2° C. in the presence of a catalytic amount of p-toluene sulfonic acid under $N_2$ blanket with agitation over a course of three hours. This reaction mixture was then cooled down to ambient temperature. Approximately 22.0 g of basic copper (II) carbonate $(CuCO_3.Cu(OH)_2, 0.1 mol)$ was added to this semi-solid mixture and this resulting mixture was refluxed at 120° C. over a course of five hours. The volatiles (water and solvent) were removed by vacuum distillation, leaving 404 g of the product as a viscous, greenish material containing 5.44% sulfur (Theory: 5.54%) and 2.6% copper (Theory: 3.1%).

EXAMPLE 3

Approximately 356 g of glycerol monooleate (commercially obtained as Kessco glycerol oleate, 1.0 mol), 89 g of 3,3'-thiodipropionic acid (0.5 mol), 300 ml of toluene, and a catalytic amount of para-toluene sulfonic acid were charged to a two liter glass reactor equipped with heater, agitator and provision for nitrogen blanketing. The reactants were heated to about 120° C. and held for twenty-one hours, until water evolution during azeotropic distillation ceased (approximately 9.5 g water was collected). Approximately 22.0 g of basic copper (II) carbonate (0.1 mol) was added to this semi-solid mixture after it was cooled down to ambient temperature. The mixture was further reacted at 120° C. over a course of six hours, until water evolution ceased (approximately 3.5 g water was collected). Vaccum was applied to remove the volatiles and this gave 426 g of deep green, viscous material.

EXAMPLE 4

Approximately 620.3 g of glycerol dioleate (commercially obtained as Kessco glycerol dioleate 1.0 mol), 300 ml toluene, 89 g of 3,3'-thiodipropionic acid (0.5 mol), and a catalytic amount of p-toluenesulfonic acid were charged to a glass reactor and heated at 120±2° C. for six hours until water evolution during azeotropic distillation ceased (approximately 9 g water was collected). The reaction mixture was then cooled down to ambient temperature, and approximately 22.0 g of basic copper (II) carbonate (0.1 mol) was added to the mixture. The reactants were heated to about 120° C. and held for five more hours, until the completion of water evolution (approximately 5.4 g water was collected). Then the solvent was removed by vacuum distillation, leaving 770 g of the product as a viscous greenish, semi-solid material.

The products of the examples were blended into fully formulated oils and evaluated by Catalytic Oxidation Test at 325° F. for forty hours (Table 1) and at 375° F. for twenty-four hours (Table 2). A comparison of the oxidation-inhibiting characteristics of the inventive products with the thiodipropionic acid derivatives, such as dilauryl thiodipropionate in fully formulated oils is also included in Table 1.

The above referred to Catalytic Oxidation Tests are substantially the same except for the indicated times and temperatures. The additives, in accordance with the invention, were blended into the respective base oils. The oils were then subjected to a stream of air at the rate of 5 liters per hour at a temperature of 325° F. for 40 hours and 375° F. for 24 hours respectively in the presence of metals having pro-oxidant properties: iron, copper, lead and aluminum. The compositions were evaluated for (1) any change in acidity or neutralization number as measured by ASTM D-974, and (2) any change in kinematic viscosity at 210° F.

EVALUATION OF PRODUCTS

TABLE 1

EVALUATION OF PRODUCTS (325° F. for 40 Hours)

| Item | Additive Conc. (Wt. %) | Change in Acid Number | % Change in Viscosity KV @ 210° F. |
|---|---|---|---|
| Base Oil (150 second, fully formulated, solvent refined paraffinic bright oil containing defoamant/demulsifier/antiwear/anticorrosion/EP/antirust performance package | — | 2.58 | 30.61 |
| Cupric Salt (Example 1) | 0.01 | 2.01 | 28.65 |
|  | 0.05 | 1.21 | 24.67 |
| Cupric Salt (Example 2) | 0.50 | 2.46 | 25.62 |
| Thioester antioxidant - DLTDP (Di-lauryl thiodipropionate) | 1.0 | 2.14 | 28.71 |
| Thioester antioxidant - DTTDP (Di-tridecyl thiodipropionate) | 0.5 | 2.13 | 30.75 |

It is to be noted that as little as 0.01%–0.5% in a fully formulated mineral oil based gear oil of the products of Examples 1 and 2 controls the increase in viscosity and total acid number of the test oil much better than equal or greater concentrations of non-copper antioxidants as shown in Table 1.

TABLE 2

(375° F. for 24 Hours)

|  | Additive Conc. (Wt. %) | KV at 100° C. New Oil | Acid Number New Oil | KV at 100° C. Used Oil | Acid Number Used Oil | Change in Acid Number | Percent Change in Viscosity KV |
|---|---|---|---|---|---|---|---|
| Base Oil (fully formulated mineral oil containing) defoamant/demulsifier/antiwear/anticorrosion/EP/antirust performance package | — | 29.06 | 1.15 | 80.74 | 7.68 | 6.53 | 177.9 |
| Cupric Salt (Example 2) | 0.5 | 29.23 | 1.54 | 57.62 | 6.96 | 5.42 | 97.1 |
| Cupric Salt (Example 3) | 0.5 | 28.97 | 1.38 | 56.87 | 6.79 | 5.41 | 96.3 |
| Cupric Salt (Example 4) | 0.5 | 28.83 | 1.74 | 59.93 | 6.79 | 5.05 | 107.9 |

The products of Examples 2, 3 and 4 also show excellent control of oxidative stability in the fully formulated mineral oil based gear oil in high temperature applications as shown in Table 2.

These data clearly demonstrate that the use of additive concentrations of thiodipropionate derived copper salts in premium quality automotive and industrial lubricants will significantly enhance their stability and extend their service life. These novel compositions are useful at low concentrations and do not contain any potentially undesirable phosphorus. These multifunctional antioxidants can be commercially made using economically favorable processes which can be readily implemented using known technology in existing equipment.

What is claimed is:

1. An improved lubricant composition comprising a minor amount of a copper salt of a thiodipropionic acid derivative or mixtures thereof sufficient to impart multifunctional/antioxidant characteristics thereto and a major amount of a lubricant comprising anoil of lubricating viscosity or grease or other solid lubricant prepared therefrom.

2. The composition of claim 1 wherein the thiodipropionic acid derivative has the following generalized structure:

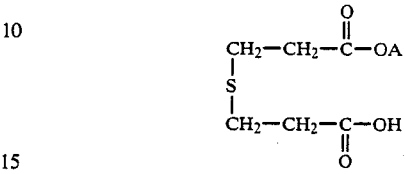

where A is hydrogen or $C_1$ to about $C_{30}$ hydrocarbyl, and where hydrocarbyl is selected from the group consisting of aralkyl, cycloalkyl, hydrocarbyl containing unsaturated vinyl, acetylene, nitrogen, oxygen, and sulfur and hetero groups containing nitrogen, oxygen or sulfur.

3. The composition of claim 2 wherein said acid derivative is derived from 3,3'-thiodipropionic acid.

4. The composition of claim 2 wherein said acid derivative is derived from 3,3'-thiodipropionic acid and oleyl alcohol.

5. The composition of claim 2 wherein said acid derivative is derived from 3,3'-thiodipropionic acid and glycerol monooleate.

6. The composition of claim 2 wherein said acid derivative is derived from 3,3'-thiodipropionic acid and glycerol dioleate.

7. The composition of claim 1 wherein said oil of lubricating viscosity is selected from the group consisting of mineral oils, synthetic oils and mixtures of mineral and synthetic oils.

8. The composition of claim 7 wherein said oil is a mineral oil.

9. The composition of claim 7 wherein said oil is a synthetic oil.

10. The composition of claim 1 wherein said oil of lubricating viscosity is a gear oil.

11. The composition of claim 1 wherein said oil of lubricating viscosity is a grease.

12. An improved lubricant composition comprising a major amount of an oil of lubricating viscosity or grease or other solid lubricant prepared therefrom and a minor effective amount of a multifunctional/antioxidant additive wherein said additive is prepared by reacting a suitable thiodipropionic acid deriviate or mixtures thereof with a suitable alcohol or amine containing compound.

13. The composition of claim 12 where the thiodipropionic acid derivative reactant is derived from 3,3'-thiodipropionic acid and a member of the group consisting of glycerol monooleate, glycerol dioleate, and oleyl alcohol.

* * * * *